(12) United States Patent
Henegar

(10) Patent No.: US 6,689,901 B2
(45) Date of Patent: Feb. 10, 2004

(54) PROCESS AND INTERMEDIATES TO PREPARE LATANOPROST

(75) Inventor: Kevin E. Henegar, Portage, MI (US)

(73) Assignee: Pharmacia & Upjohn Company, Kalamazoo, MI (US)

(*) Notice: Subject to any disclaimer, the term of this patent is extended or adjusted under 35 U.S.C. 154(b) by 38 days.

(21) Appl. No.: 10/179,499

(22) Filed: Jun. 25, 2002

(65) Prior Publication Data

US 2003/0045571 A1 Mar. 6, 2003

Related U.S. Application Data

(60) Provisional application No. 60/306,026, filed on Jul. 17, 2001.

(51) Int. Cl.[7] .............................................. C07C 59/00
(52) U.S. Cl. ........................................ 562/465; 514/530
(58) Field of Search ........................... 562/465; 514/530

(56) References Cited

U.S. PATENT DOCUMENTS

| | | |
|---|---|---|
| 5,296,504 A | 3/1994 | Stjernschantz et al. ..... 514/550 |
| 5,422,368 A | 6/1995 | Stjernschantz et al. ..... 514/530 |

FOREIGN PATENT DOCUMENTS

| | | | |
|---|---|---|---|
| WO | 98/30900 | | 7/1998 |
| WO | WO 2001087816 | * | 11/2001 |

OTHER PUBLICATIONS

*J. Am. Chem. Soc.*, 110(5), 1539–46 (1988).
*Bull. Korean Chem. Soc.*, 15(12), 1033–4 (1994).
*Tetrahedron Letters*, 1067–1070 (1976).
*J. Am. Chem. Soc.*, 92 (2), 397–8 (1970).
*J. Am. Chem. Soc.*, 96(18), 5865–76 (1974).

\* cited by examiner

*Primary Examiner*—Alan L. Rotman
*Assistant Examiner*—Hector M. Reyes
(74) *Attorney, Agent, or Firm*—John H. Engelmann

(57) ABSTRACT

The present invention is a novel intermediate, compound of the formula (VI)

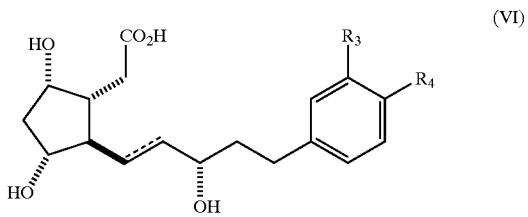

and salts thereof. In addition, the invention includes a process for the preparation of a 15(S)-prostaglandin intermediates compounds (IV) and (XVIII) which comprises (1) contacting a the corresponding enone with (−)-chlorodiisopinocampheylborane while maintaining the reaction mixture temperature in the range of from about −50° to about 0° and (2) contacting the reaction mixture of step (1) with a boron complexing agent.

23 Claims, No Drawings

PROCESS AND INTERMEDIATES TO PREPARE LATANOPROST

CROSS-REFERENCE TO RELATED APPLICATIONS

This patent application claims priority of invention under 35 U.S.C. §119(e) from U.S. provisional patent application Serial No. 60/306,026, filed Jul. 17, 2001.

BACKGROUND OF THE INVENTION

1. Field of the Invention

The present invention is a process, including intermediates, to produce latanoprost, a pharmaceutical agent useful in treating ophthalmic conditions.

2. Description of the Related Art

U.S. Pat. No. 5,422,368 discloses latanoprost (Example 2) and its usefulness as an ophthalmic agent. The patent discloses a process (Example 2) to prepare latanoprost and two closely related compounds.

There are very limited numbers of examples of reductions of α,β-unsaturated enones with chlorodiisopinocampheylborane. *J. Am. Chem. Soc.*, 110(5), 1539–46 (1988) describes a single example of reduction of an acyclic aryl enone, 4-phenyl-3-buten-2-one, with chlorodiisopinocampheylborane giving an 81% eantiomeric selectivity, and no examples of simple acyclic non-aryl conjugated enones.

*Bull. Korean Chem. Soc.*, 15(12), 1033–4 (1994) addresses the issue of 1,2 versus 1,4 reduction with chlorodiisopinocampheylborane but did not discuss the enantioselectivity or diastereoselectivity of the reductions.

*Tetrahedron Letters* 1067–1070 (1976) discloses a cyclopentane diol-acid where the side-chain did not contain any aromatic functionality.

SUMMARY OF INVENTION

Disclosed is a compound of the formula (VI)

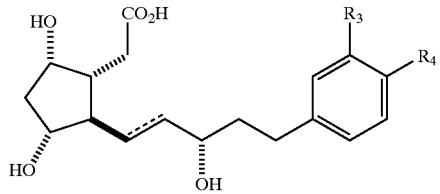

(VI)

where:
- (1) $R_3$ is —H and $R_4$ is —H,
- (2) $R_3$ is —H and $R_4$ is —O—$CH_3$ and
- (3) $R_3$ and $R_4$ are taken together to form a five member ring attached to the 3- and 4-positions of the phenyl ring where the second ring from the $R_3$-position to the $R_4$-position is —CH=CH—O— and
  where ... is a single or double bond and pharmaceutically acceptable salts thereof.

Also disclosed is a process for the preparation of a 15(S)-prostaglandin intermediate selected from the group consisting of compound (IV)

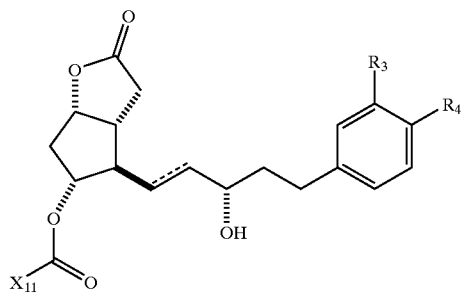

(IV)

where $R_3$, $R_4$ and ... are as defined above and where $X_{11}$ is phenyl or phenyl substituted with one thru three $C_1$–$C_4$ alkyl, one thru three $C_1$–$C_4$ alkoxy, one phenyl, one thru three —F, —Cl, —Br and —I and compound (XVIII)

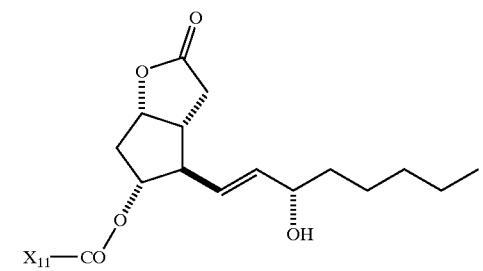

where $X_{11}$ is defined above which comprises:
(1) contacting a compound selected from the group consisting of compound (III)

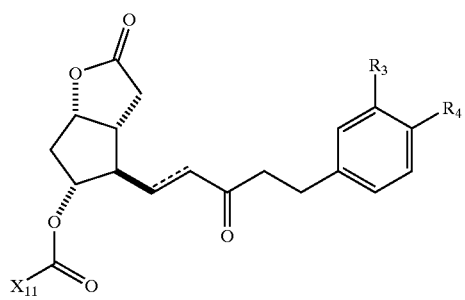

(III)

where $R_3$, $R_4$, $X_{11}$ and ... are as defined above or compound (XVII), respectively,

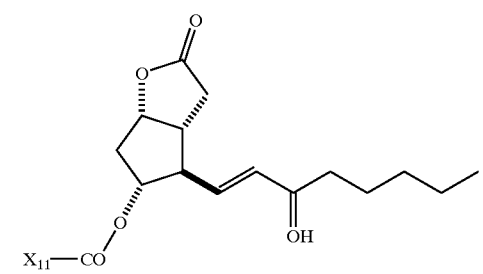

where $X_{11}$ is defined above with (−)-chlorodiisopinocampheylborane while maintaining the reaction mixture temperature in the range of from about −50° to about 0° and (2) contacting the reaction mixture of step (1) with a boron complexing agent.

DETAILED DESCRIPTION OF THE INVENTION

Latanoprost (XVI) is known, see U.S. Pat. No. 5,422,368, Example 2.

The process of the present invention is set fort in CHARTs A and B and in EXAMPLES 1–12.

The enone (III), as well as the other compounds of the invention, has three possibilities for the substitution on the phenyl ring of the bottom side chain. These are where $R_3$ and $R_4$ are:

(1) $R_3$ is —H and $R_4$ is —H which gives phenyl,
(2) $R_3$ is —H and $R_4$ is —O—$CH_3$ which give 4-methoxyphenyl and
(3) $R_3$ and $R_4$ are taken together to form a five member ring attached to the 3- and 4-positions of the phenyl ring where the second ring from the $R_3$-position to the $R_4$-position is —CH=CH—O—;
where ... is a single or double bond and
where $X_{11}$ is phenyl or phenyl substituted with one thru three $C_1$–$C_4$ alkyl, one thru three $C_1$–$C_4$ alkoxy, one phenyl, one thru three —F, —Cl and —Br. It is preferred that $R_3$ and $R_4$ are both —H. It is preferred that $X_{11}$ is phenyl.

The enone (III) must be protected at the C-11 position as is known to those skilled in the art. It is preferred that for the protecting group —CO—$X_{11}$, $X_{11}$ is phenyl or phenyl substituted with one thru three $C_1$–$C_4$ alkyl, one thru three $C_1$–$C_4$ alkoxy, one phenyl, one thru three —F, —Cl and —Br. With regard to the (–)-chlorodiisopinocampheylborane reduction of the α,β-unsaturated enone (III) the reduction can be performed in any chemically inert solvent that adequately dissolves the enone (III). Suitable solvents include THF, methylene chloride and DME and mixtures thereof. MTBE and toluene alone are not operable. The use of a cosolvent, such as hexane, heptane, isooctane or similar hydrocarbons is not necessary but is preferred. This is important since (–)-chlorodiisopinocampheylborane is available commercially as a solution in these solvents. MTBE and toluene can be used as the cosolvent. The nature of the solvent has virtually no effect with regard to the 15(S)/15(R) ratio in the product. It is preferred that from about 3 to about 4 equivalents of (–)-chlorodiisopinocampheylborane be used; it is more preferred that at least 3.5 equivalents of (–)-chlorodiisopinocampheylborane be used. With fewer equivalents the reaction is incomplete; there is no improvement in rate or selectivity with more equivalents. When the (–)-chlorodiisopinocampheylborane is contacted with the α,β-unsaturated enone (III), the temperature should be maintained less than 0°. It is preferred that the temperature be maintained at less than –20°; it is more preferred that the temperature be maintained in the range of from about –35 to about –45°. Above –35° the selectivity decreases and below about –45° the rate becomes too slow to be practical.

When the reaction is complete, the excess (–)-chlorodiisopinocampheylborane must be destroyed by use of a boron complexing agent which is selected from the group consisting of water, $C_1$–$C_6$ alcohols and diols, ethanolamine, diethanolamine, triethanolamine and mixtures thereof. It is preferred that the boron complexing agent be group be water and diethanolamine; it is more preferred that the complexing agent be water.

It is preferred that prior to step (2), the reaction mixture of step (1) is contacted with a readily reducible aldehyde or ketone. It is preferred that the readily reducible aldehyde or ketone is selected from the group consisting of $C_1$–$C_6$ aldehydes and ketones and benzaldehyde; it is more preferred that the readily reducible aldehyde or ketone is acetone or methylethylketone. When adding the boron complexing agent it is preferred that a base also be added. It is preferred that the base is selected from the group consisting of carbonate, bicarbonate, mono- di- and tri-$C_1$–$C_6$ alkylamines, pyridine and pyridine substituted with $C_1$–$C_4$ alkyl; it is more preferred that the base be bicarbonate or carbonate. It is even more preferred that the base be bicarbonate.

Either prior to, or after, step (2), it is preferred to warm the reaction mixture to about 15 to about 25°. It is preferred that the reaction mixture is warmed from about 1 to about 3 hr.

Latanoprost (XVI) is known to be useful as an ophthalmic pharmaceutical agent, see U.S. Pat. Nos. 5,296,504 and 5,422,368. In addition, International Publication WO98/30900 discloses that latanoprost (XVI) is useful in treating another ophthalmic condition, myopia.

The process of CHART B (and EXAMPLEs 11 & 12) starts with a known enone (XVII) and transforms it to the 15-alcohol (XVIII) intermediate known to be useful in the production of pharmaceutically useful prostaglandins, see *Tetrahedron Letters*, 1076–1070 (1976) and *J. Am. Chem. Soc.* 92, 397–8 (1970). The process of the reduction of the non-aryl α,β-unsaturated ketone (XVII) is analogous to the reduction of the aryl α,β-unsaturated ketone (III).

The products where $R_3$ is —H and $R_4$ is —O—$CH_3$ and where $R_3$ and $R_4$ are taken together to form a five member ring attached to the 3- and 4-positions of the phenyl ring where the second ring from the $R_3$-position to the $R_4$-position is —CH—CH—O— are also known to be useful pharmaceutical agents. Those two agents can also be prepared by the process of the present invention.

Definitions and Conventions

The definitions and explanations below are for the terms as used throughout this entire document including both the specification and the claims.

Definitions

All temperatures are in degrees Celsius.

Latanoprost (XVI) refers to (5Z)-(9CI)-7-[(1R,2R,3R,5S)-3,5-dihydroxy-2-[(3R)-3-hydroxy-5-phenylpentyl]cyclopentyl]-5-heptenoic acid 1-methylethyl ester. It is also known as 17-phenyl-18,19,20-trinor-$PF_{2\alpha}$ isopropyl ester.

MTBE refers to methyl t-butyl ether.

TLC refers to thin-layer chromatography.

THF refers to tetrahydrofuran.

THP refers to tetrahydropyranyl.

Saline refers to an aqueous saturated sodium chloride solution.

Chromatography (column and flash chromatography) refers to purification/separation of compounds expressed as (support, eluent). It is understood that the appropriate fractions are pooled and concentrated to give the desired compound(s).

CMR refers to C-13 magnetic resonance spectroscopy, chemical shifts are reported in ppm (δ) downfield from TMS.

NMR refers to nuclear (proton) magnetic resonance spectroscopy, chemical shifts are reported in ppm (δ) downfield from tetramethylsilane.

TMS refers to trimethylsilyl.

–φ refers to phenyl ($C_6H_5$).

MS refers to mass spectrometry expressed as m/e, m/z or mass/charge unit. [M+H]+ refers to the positive ion of a parent plus a hydrogen atom. EI refers to electron impact. CI refers to chemical ionization. FAB refers to fast atom bombardment.

HRMS refers to high resolution mass spectrometry.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

psi refers to pounds per square inch.

When solvent pairs are used, the ratios of solvents used are volume/volume (v/v).

When the solubility of a solid in a solvent is used the ratio of the solid to the solvent is weight/volume (wt/v).

DIBAL refers to diisobutyl aluminum hydride.

THAM refers to tris(hydroxymethyl)aminomethane.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

Preparation 1

Potassium 5-(triphenylphosphoranylidene)pentaonate

4-Carboxybutyltriphenylphosphonium bromide (2.91 g) is stirred with THF (10 mL) and the slurry cooled to 0°. Potassium t-butoxide (20% w/v, 7.6 mL) solution in THF is cooled to 0°. The butoxide solution is added to the slurry dropwise maintaining the temperature at 0 to 5° and then stirring for 1 hour. The resulting ylide solution is then cooled to –10°.

Example 1

[3aR-[3aα,4α(E),5β,6aα]]-5-(benzoyloxy) hexahydro-4-(3-oxo-5-phenyl-1-pentenyl)-2H-cyclopenta[b]furan-2-one (III)

Lithium chloride (2.6 g) is dissolved in THF (170 mL). Dimethyl (2-oxo-4-phenylbutyl)phosphonate (II, 7.87 g) and triethylamine (4.3 mL) are added. The mixture is stirred and cooled to –10°. A solution of the Corey aldehyde benzoate, (1S,5R,6R,7R)-6-formyl-7-(benzyloxy)-2-oxabicyclo[3.3.0]octan-3-one (I, 8.42 g) in THF (75 mL) is added to the reaction mixture over three hours. The resulting mixture is stirred for 18 hours at –10°. At the end of this time, MTBE (100 mL) is added and the mixture warmed to 0 to +20°. Sodium bisulfite (38%, 100 mL) is added and the two-phase mixture was stirred for 10 min. The phases are separated and the organic phase is washed with saturated aqueous sodium bicarbonate solution (100 mL). The organic phase is separated and concentrated under reduced pressure to a volume of <100 mL. Ethyl acetate (200 mL) is added and the mixture is concentrated to a volume of 50 mL. MTBE (100 mL) is added and the mixture is allowed to cool to 20–25 deg for 1 hour. The mixture is then cooled to –20° for 2 hours. The solids were filtered, washed with MTBE and dried on a nitrogen press to give the title compound, mp=117–118°; NMR ($CDCl_3$, 400 MHz) δ 7.82, 7.41, 7.28, 7.10, 7.02, 6.49, 6.04, 5.12, 4.91, 2.72 and 2.5–2.1; CMR ($CDCl_3$, 100.6 MHz) δ 198.5, 175.7, 165.8, 143.0, 140.8, 133.5, 131.4, 129.4, 128.5, 126.2, 83.0, 78.4, 54.0, 42.5, 37.8, 34.8 and 29.9.

Example 2

[3aR-[3aα,4a(1E,3S*),5β,6aα]]-5-(Benzoyloxy) hexahydro-4-(3-hydroxy-5-phenyl-1-pentenyl)-2H-cyclopenta[b]furan-2-one (IV)

A mixture of [3aR-[3aα,4α(E),5β,6aβ]]-5-(benzoyloxy) hexahydro-4-(3-oxo-5-phenyl-1-pentenyl)-2H-cyclopenta [b]furan-2-one (III, EXAMPLE 1, 10.0 g, 0.0247 mole) in THF (100 mL) is cooled to –38 to –42°. A solution of (–)-chlorodiisopinocampheylborane (2M in hexane; 43 mL) is added to the enone (III) mixture maintaining the internal temperature at less than –35°. When the addition is complete, the mixture is stirred at –38 to –42° for 18 hours. At this time acetone (12.7 mL) is added and the mixture is allowed to warm to 20–25° and stirred for two hours. MTBE (100 mL) is added and then a solution of sodium bicarbonate (10 g) in water (150 mL) is added. The two phase mixture is stirred for 15 min. The phases are separated and the organic phase is washed with water (100 mL). The organic phase is concentrated under reduced pressure. MTBE (300 mL) is added and the mixture then concentrated. Acetonitrile (100 mL) is added and the mixture is again concentrated. Acetonitrile (150 mL) and heptane (100 mL) are added. The two-phase mixture is stirred for 5 min and then allowed to settle. The phases are separated. The acetonitrile phase is extracted with heptane (3×100 mL). The acetonitrile phase is concentrated. A portion of the concentrate is removed and purified by chromatography (silica gel, 230–400 mesh; heptane/ethyl acetate, 1/1) to give the title compound, mp=78–81°; NMR ($CDCl_3$, 400 MHz) δ 7.77, 7.32, 7.19, 7.04, 6.94, 5.45, 5.37, 5.01, 4.79, 3.88, 2.61–2.23, 2.01 and 1.60; CMR ($CDCl_3$, 100.6 MHz) δ 176.5, 166.0, 141.7, 136.0, 133.3, 129.5, 128.4, 125.8, 83.3, 79.2, 71.2, 53.9, 42.6, 38.7, 37.5, 34.9 and 31.5.

Example 3

[3aR-[3aα,4a(1E,3S*),5β,6aα]]-5-(Benzoyloxy) hexahydro-4-(3-hydroxy-5-phenyl-1-pentyl)-2H-cyclopenta[b]furan-2-one (V)

[3aR-[3a α,4a(1E,3S*),5β,6aα]]-5-(benzoyloxy) hexahydro-4-(3-hydroxy-5-phenyl-1-pentenyl)-2H-cyclopenta[b]furan-2-one (IV, EXAMPLE 2) is dissolved in THF (125 mL). Platinum on carbon catalyst (5%, 1 g) and triethylamine (3.4 mL) are added. The mixture is purged with nitrogen and then and the mixture is stirred vigorously under 5 psi hydrogen at 20°±5°. When the reaction was complete as measured by HPLC, the reaction is purged with nitrogen. The mixture is filtered over celite. The filtrate is concentrated under reduced pressure to give the crude product. A portion of the product is removed and purified by chromatography (silica gel, 230–400 mesh; heptane/ethyl acetate, 1/1) to give the title compound, mp=68–70°; NMR ($CDCl_3$, 400 MHz) δ 7.91, 7.47, 7.36, 7.19, 7.10, 5.18, 4.99, 3.56, 2.84–2.57, 2.44–2.26, 1.71–1.16; CMR ($CDCl_3$, 100.6 MHz) δ 176.9, 166.0, 141.8, 133.2, 129.6, 128.4, 125.9, 84.4, 80.1, 70.8, 52.6, 43.5, 39.0, 37.7, 36.2, 35.1, 32.0 and 29.5; MS calculated m/z=408, found m/z=409 (m+1).

Example 4

2-[(1R, 2R, 3R, 5S)-3,5-Dihydroxy-2-[(3R)-3-hydroxy-5-phenylpentyl]cyclopentyl]acetic Acid (VI)

A mixture of potassium hydroxide (10) in methanol (300 ml) and water (5 mL) is added to [3aR-[3aα,4a(1E,3S*),5β, 6aα]]-5-(benzoyloxy)hexahydro-4-(3-hydroxy-5-phenyl-1-pentyl)-2H-cyclopenta[b]furan-2-one (V, EXAMPLE 3). The mixture is stirred and heated in an 80° oil bath for about 2 hours. When the reaction is complete, the mixture is concentrated under reduced pressure. Water (100 mL) and MTBE (100 mL) are added and the mixture stirred at 20–25° for 15 min. The phases are allowed to separate. The product is in the aqueous phase and the organic phase is removed and discarded. The pH of the aqueous phase is adjusted to 1 to 1.5 by the addition of hydrochloric acid (3 N, about 60 mL are required). The solution is stirred at 20–25°. After 30 min, MTBE (100 mL) is added and the mixture stirred at 20–25° for about 12 hours. The phases are separated and the aqueous phase extracted once with MTBE (50 mL). The MTBE phases are combined and washed with sodium carbonate (1 N, 50 mL). The MTBE mixture is stirred with a solution of potassium hydroxide (2.8 g, 42.5 mmole) in water (100 mL) for 30 min. The phases are separated and the aqueous phase is added to a slurry of citric acid monohydrate (8.90 g) and ethyl acetate (100 mL) at 20–25 deg. The mixture is stirred for 15 min and the phases are separated. The aqueous phase is extracted with ethyl acetate (5×50 mL). The combined organic phases are dried over anhydrous sodium sulfate (8.90 g) for 15 min. The ethyl acetate extract is concentrated under reduced pressure to a volume of 100 mL maintaining the internal temperature less than 300. Ethyl acetate (200 mL) is added and the mixture is again concentrated to a volume of 100 mL. The resulting slurry is stirred at 0–5° for 30 min. The solids are filtered and washed with heptane/ethyl acetate (1/1, 35 mL), then dried on a nitrogen press to give the title compound.

Example 5

[3aR-[3aα,4α(R*),5β,6aα]]-Hexahydro-5-hydroxy-4-(3-hydroxy-5-phenylpentyl)-2H-cyclopenta[b]furan-2-one (VII)

2-[(1R, 2R, 3R, 5S)-3,5-Dihydroxy-2-[(3R)-3-hydroxy-5-phenylpentyl]cyclopentyl]acetic acid (VI, EXAMPLE 4, 4.80 g) and toluene (100 mL) are stirred and the slurry heated to reflux for 30 min. After 30 min, the toluene is slowly distilled at atmospheric pressure to remove water. After about 1 hour of distillation, all the hydroxy acid has dissolved. The solution is then distilled to a volume of about 50 mL. The mixture is then cooled to about 800 and ethyl acetate (25 mL) is added. The mixture is then cooled to about 30° and heptane (20 mL) is added. The mixture is seeded with a small amount of the title compound. The mixture is stirred at about 30° for 10 min, during which time massive crystallization occurred. After the product had crystallized, heptane (30 mL) is added over 15 min. The slurry is cooled to 20–25° and stirred for 1 hour. The product is filtered and dried under nitrogen to give the title compound, mp=69–71°; NMR (CDCl$_3$, 400 MHz) δ 7.35, 7.26, 5.00, 4.06, 3.68, 2.89–2.55, 2.34–2.07 and 1.87–1.34; CMR (CDCl$_3$, 100.6 MHz) δ 177.8, 141.9, 128.4, 125.9, 84.0, 71.2, 53.9, 43.1, 41.4, 39.1, 36.0, 35.2, 32.0 and 28.9.

Example 6

(3aR,4R,5R,6aS)-5-(1-Ethoxyethoxy)-4-[(3R)-3-(1-ethoxyethoxy)-5-phenylpentyl]hexahydro-2H-cyclopenta[b]furan-2-one (X)

[3aR-[3aα,4α(R*),5β,6aα]]-Hexahydro-5-hydroxy-4-(3-hydroxy-5-phenylpentyl)-2H-cyclopenta[b]furan-2-one (VII, EXAMPLE 5, 1.0 g, 3.3 mmoles) is dissolved in methylene chloride (3 mL) and the mixture is placed in a sealable pressure tube. Add 1.0 mL of a mixture of trichloracetic acid (0.27 g) in methylene chloride (10 mL) followed by ethyl vinyl ether (6.3 mL). The pressure tube is closed and heated to 45° in an oil bath for about 8 hours. At this time, triethylamine (0.12 mL) is added and the mixture is stirred for 10 minutes. The mixture is then concentrated under reduced pressure.

Example 7

(3aR,4R,5R,6aS)-5-(1-Ethoxyethoxy)-4-[(3R)-3-(1-ethoxyethoxy)-5-phenylpentyl]hexahydro-2H-cyclopenta[b]furan-2-ol (XI)

(3aR,4R,5R,6aS)-5-(1-Ethoxyethoxy)-4-[(3R)-3-(1-ethoxyethoxy)-5-phenylpentyl]hexahydro-2H-cyclopenta[b]furan-2-one (X, EXAMPLE 6) is dissolved in THF (14 mL) and the mixture cooled to −40°. Using a syringe pump, DIBAL (1.0 M, 3.78 mL in toluene) is added over 15 minutes, maintaining the internal temperature at less than −30°. The mixture is stirred for 15 minutes after the completion of the addition, then ethyl acetate (0.38 mL) is added. The mixture is poured into a solution of potassium sodium tartarate (10 g in 30 mL of water) and warmed to 20–25°. The two phase mixture is heated to 45° for 1 hr and then cooled. The phases are separated and the organic phase is concentrated.

Example 8

7-[(1R,2R,3R,5S)-3-(1-Ethoxyethoxy)-5-hydroxy-2-[(3R)-3-(1-ethoxyethoxy)-5-phenylpentyl]cyclopentyl-5-heptenoic Acid (XII)

(3aR,4R,5R,6aS)-5-(1-Ethoxyethoxy)-4-[(3R)-3-(1-ethoxyethoxy)-5-phenylpentyl]hexahydro-2H-cyclopenta[b]furan-2-ol (XI, EXAMPLE 7) is dissolved in dry THF (10 mL) and added to a mixture containing potassium 5-(triphenylphosphoranylidene)pentaonate (PREPARATION 1) solution at −10° to −5°. The resulting mixture is stirred for about 3 hours at less than −5°. Water (30 mL; 0°) is added over 10 minutes, then ethyl acetate (20 mL) and aqueous THAM solution (10 mL) is added. The phases are separated and the organic phase is washed with aqueous THAM solution (15%, 2×15 mL). The aqueous phases are combined and washed once with ethyl acetate (15 mL). MTBE (50 mL) is added to the combined aqueous phases. The mixture is acidified to pH=3 with aqueous phosphoric acid (40%). The organic phase is separated and concentrated under reduced pressure to 20 mL. Solids (5-diphenypphosphinopentanoic acid) crystallized. MTBE (50 mL) is added and the slurry concentrated under reduced pressure to a volume of 20 mL. The solid is filtered and washed with MTBE (100 mL). The filtrate is concentrated under reduced pressure to give the title compound.

Example 9

Latanoprost Acid; (5Z)-7-[(1R,2R,3R,5S)-3,5-Dihydroxy-2-[(3R)-3-hydroxy-5-phenylpentyl]cyclopentyl]5-heptenoic Acid (XV)

7-[(1R,2R,3R,5S)-3-(1-Ethoxyethoxy)-5-hydroxy-2-[(3R)-3-(1-ethoxyethoxy)-5-phenylpentyl]cyclopentyl-5-heptenoic acid (XII, EXAMPLE 8) is dissolved in THF (30 mL). Water (15 mL) and phosphoric acid (85 wt %; 0.67 mL) are added and the mixture is heated to reflux for about 2 hours. The mixture is cooled and MTBE (30 mL) is added. The phases are separated. The organic phase is washed once with saline (100 mL). The organic phase is concentrated under reduced pressure. MTBE (3×50 mL) is added and concentrated under reduced pressure to give the title compound.

Example 10

Latanoprost; (5Z)-(9CI)-7-[(1R,2R,3R,5S)-3,5-Dihydroxy-2-[(3R)-3-hydroxy-5-phenylpentyl]cyclopentyl]-5-heptenoic Acid 1-methylethyl Ester (XVI)

Latanoprost acid (XV, EXAMPLE 9) is dissolved in DMF (10 mL) and added to a slurry of cesium carbonate (1.6 g) in DMF (10 mL). 2-Iodopropane (0.49 mL) is added and the slurry is heated to 45° for about 6 hours. When the reaction is complete, MTBE (40 mL) and water (50 mL) are added and the mixture is stirred for 15 minutes. The phases are separated and the aqueous phase is washed with MTBE (20 mL). The organic phases are combined and concentrated. The concentrate is chromatographed (silica, 150 g, 230–400 mesh) eluting with MTBE. The appropriate fractions are pooled and concentrated to give the title compound.

Example 11

2-[(1R, 2R, 3R, 5S)-3,5-Dihydroxy-2-[(3R)-3-hydroxy-1-octenyl]cyclopentyl]acetic Acid (XIX)

(−) Chlorodiisopinocampheylborane (27.0 g) is dissolved in THF (90 mL) and cooled to −35°. A mixture of [3aR-[3aα,4α(E),5β,6aπ]]-5-(benzoyloxy)hexahydro-4-(3-oxo-1-octenyl)-2H-cyclopenta[b]furan-2-one (XVII, *J. Am. Chem. Soc.*, 96(18), 5865–76 (1974), 7.4 g) in THF (30 mL) is added maintaining the internal temperature of the mixture at <−35°. The mixture is stirred at −35 to −40° for 18 hours. Acetone (12.3 mL) is added and the solution stirred at 20–25° for 2 hours. MTBE (50 mL) and saturated aqueous sodium bicarbonate solution (50 mL) are added and the two-phase mixture is stirred for 5 min. The organic phase is separated and washed once with water (50 mL), then concentrated under reduced pressure. The mixture is stirred at reflux with methanol (75 mL), water (7.5 mL) and potassium hydroxide (4.76 g) for 2 hours. The mixture is concentrated under reduced pressure. The concentrate is partitioned between water (75 mL) and MTBE (75 mL). The aqueous phase is separated and extracted with MTBE (2×50 mL). The pH of the aqueous phase is adjusted to about 1.2 with hydrochloric acid (3 M) and stirred for 2.5 hours. The mixture is saturated with sodium chloride and then extracted with MTBE (4×75 mL). The MTBE mixtures are combined and washed with sodium carbonate solution (1 M, 2×50 mL). The sodium carbonate solutions are back extracted with MTBE (2×50 mL). The combined MTBE extracts are concentrated to a volume of about 100 mL, then stirred for one hour with a solution of potassium hydroxide (3.29 g) in water (30 mL). The aqueous phase is separated and added to a slurry of anhydrous citric acid (9.68 g) in ethyl acetate (100 mL). The phases are separated and the aqueous phase is extracted with ethyl acetate (4×50 mL). The combined ethyl acetate extracts are filtered through anhydrous sodium sulfate (about 10 g). The filtrate is concentrated under reduced pressure (30° maximum temperature) to a volume of about 100 mL. Ethyl acetate (100 mL) is added and the mixture is concentrated under reduced pressure (30° maximum temperature) to a volume of about 80 mL. The resulting slurry is cooled to −20° for one hour and then filtered, to give the title compound, mp=105–107°; NMR (d6-DMSO, 400 MHz) δ 5.37–5.49, 4.61, 4.58, 4.06, 3.94, 3.76, 2.48, 2.35, 2.11–2.16, 1.8, 1.27–1.51 and 0.94; CMR (d6-DMSO, 100.6 MHz) δ 174.48, 136.33, 131.21, 75.65, 71.40, 69.37, 53.79, 44.42, 44.31, 37.80, 31.82, 31.64, 25.16, 22.49 and 14.23.

Example 12

(3aS,4S,5S,6aR)-Hexahydro-5-hydroxy-4-[(1E,3R)-3-hydroxy-1-octenyl]-2H-Cyclopenta[b]furan-2-one (XX)

2-[(1R, 2R, 3R, 5S)-3,5-dihydroxy-2-[(3R)-3-hydroxy-1-octenyl]cyclopentyl]acetic acid (XIX, EXAMPLE 11, 2.55 g) is stirred with MTBE (100 mL) and trichloroacetic acid (0.102 g). The slurry is heated to reflux for more than one hour. Then triethylamine (0.2 mL) is added. The mixture is cooled and washed once with water (50 mL) of water. The mixture is dried over anhydrous granular sodium sulfate and then concentrated under reduced pressure to give the title compound, NMR (CDCl₃, 400 MHz) δ 5.58, 5.43, 4.88, 4.03, 3.92, 3.55, 2.8, 2.71, 2.3–2.5, 2.22, 1.9, 1.2–1.6 and 0.89; CMR (CDCl₃, 100.6 MHz) δ 176.94, 136.79, 130.20, 82.41, 76.27, 72.78, 56.12, 42.34, 39.61, 37.05, 33.98, 31.60, 25.06, 22.52 and 13.94.

CHART A

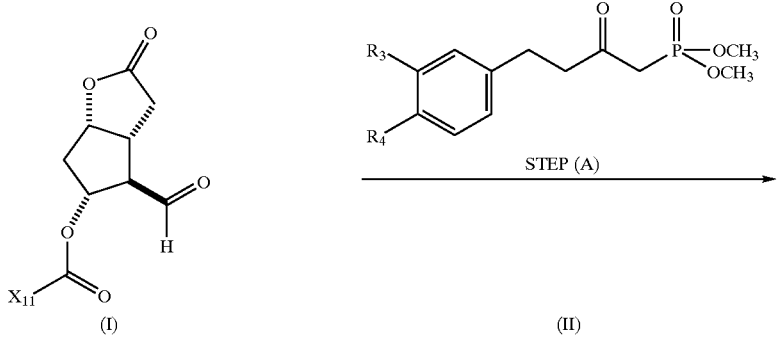

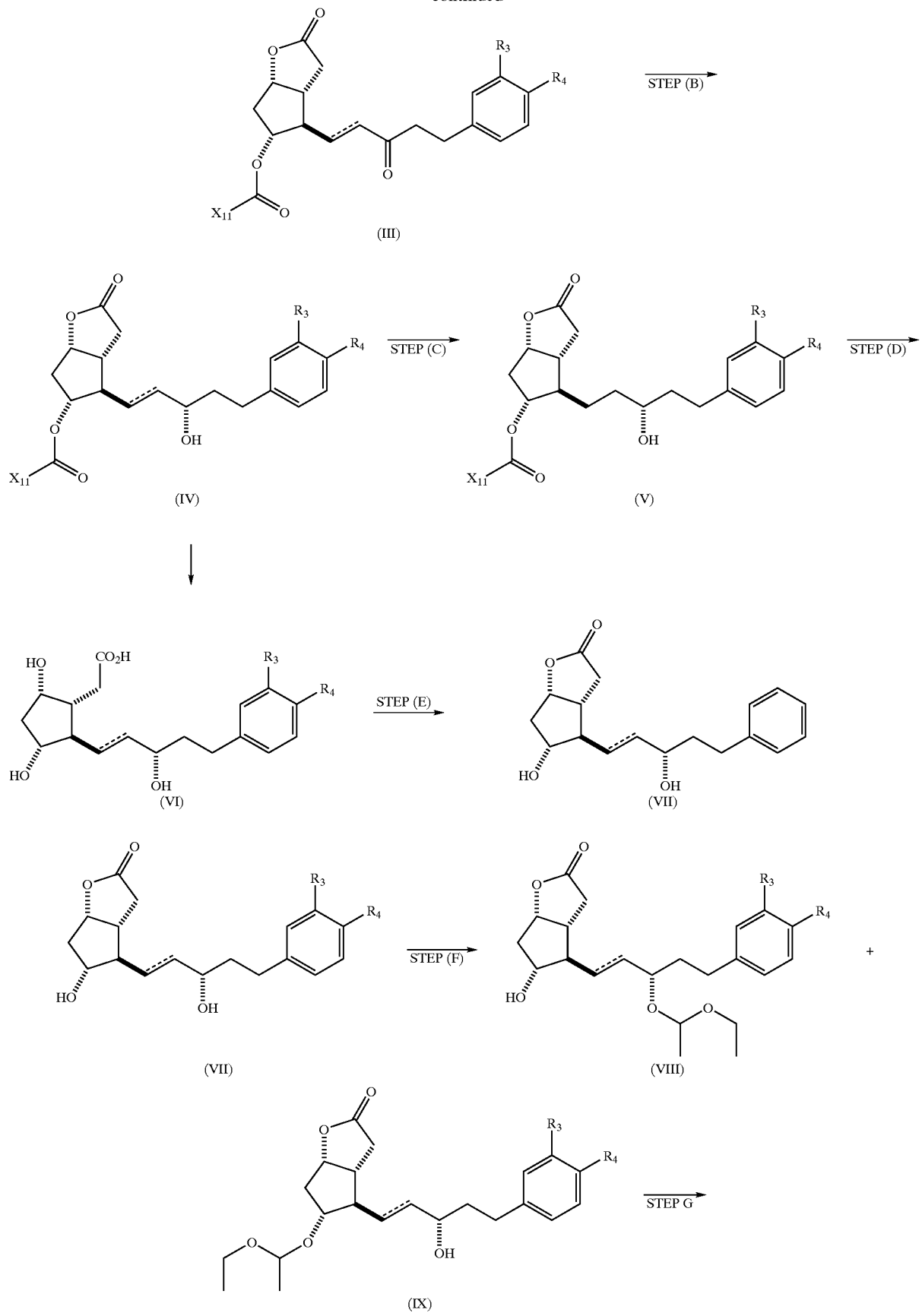

-continued
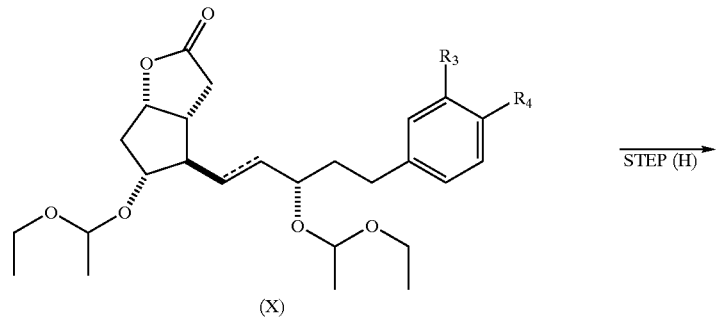
(X)
STEP (H)
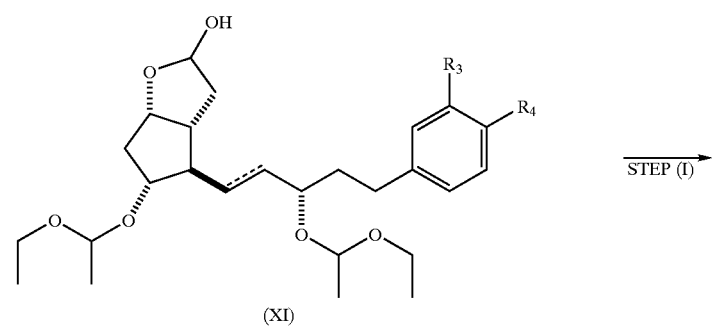
(XI)
STEP (I)
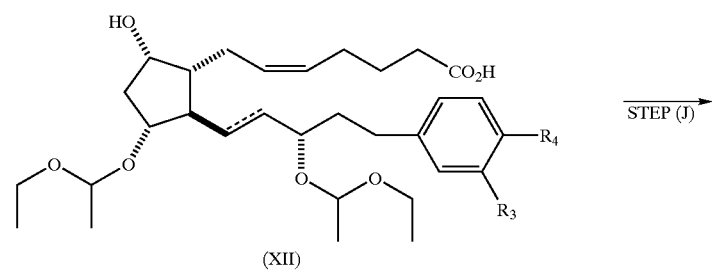
(XII)
STEP (J)
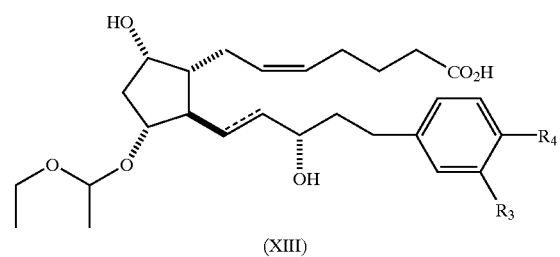
(XIII)
+
STEP (K)
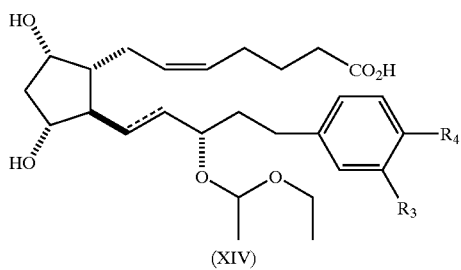
(XIV)

-continued

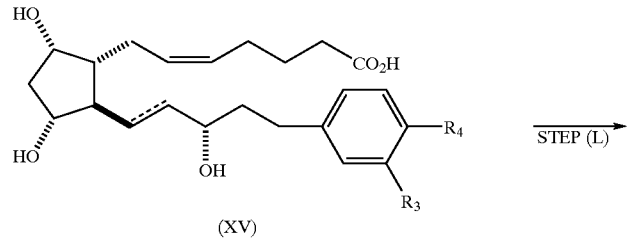

(XV)

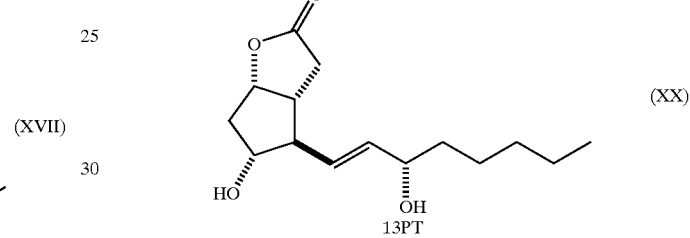

(XVI)

CHART B

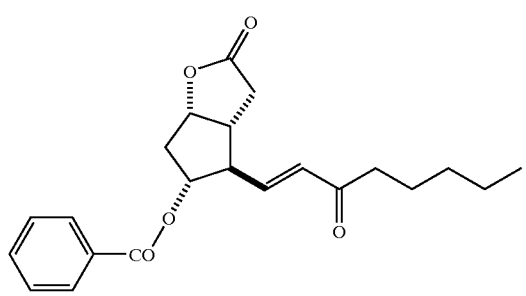

(XVII)

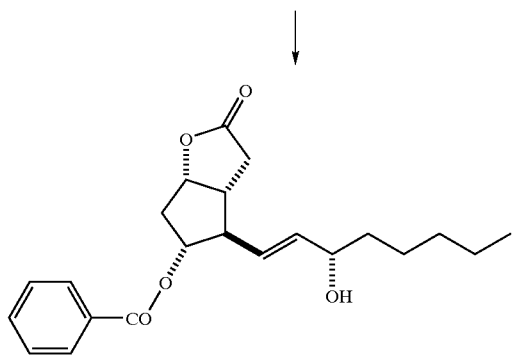

(XVIII)

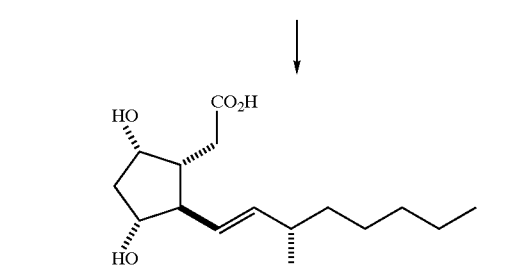

(XIX)

-continued

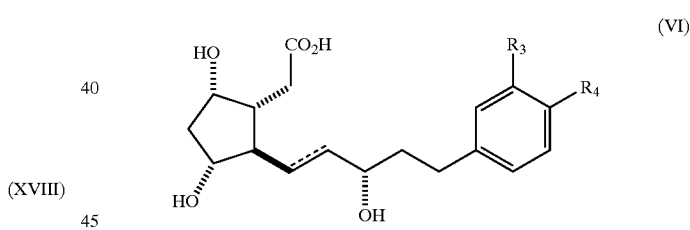

(XX)

13PT

What is claimed is:
1. A compound of the formula (VI)

where:
(1) $R_3$ is —H and $R_4$ is —H,
(2) $R_3$ is —H and $R_4$ is —O—CH$_3$ and
(3) $R_3$ and $R_4$ are taken together to form a five member ring attached to the 3- and 4-positions of the phenyl ring where the second ring from the $R_3$-position to the $R_4$-position is —CH=CH—O— and
where ⋯ is a single or double bond and pharmaceutically acceptable salts thereof.

2. A compound according to claim 1 where the cation of the salt is selected from the group consisting of sodium, potassium, lithium, cesium, $R_1R_2R_3N^+$—H where $R_1$, $R_2$ and $R_3$ are the same or different and are $C_1$–$C_4$ alkyl, α-methylbenzylamine, pyridine, pyridine substituted with $C_1$–$C_4$ alkyl, benzylamine and β-phenethylamine.

3. A compound according to claim 2 where the amine of the cation is triethylamine or pyridine.

4. A compound according to claim 1 where $R_3$ and $R_4$ are both —H and ⋯ is a single bond which is 2-[(1R, 2R, 3R, 5S)-3,5-dihydroxy-2-[(3R)-3-hydroxy-5-phenylpentyl]cyclopentyl]acetic acid.

5. A process for the preparation of a 15(S)-prostaglandin intermediate selected from the group consisting of compound (IV)

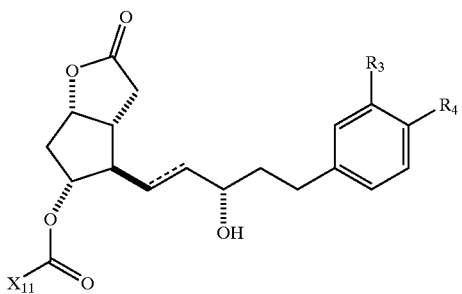

where:

(1) $R_3$ is —H and $R_4$ is —H, (2) $R_3$ is —H and $R_4$ is —O—$CH_3$ and (3) $R_3$ and $R_4$ are taken together to form a five member ring attached to the 3- and 4-positions of the phenyl ring where the second ring from the $R_3$-position to the $R_4$-position is —CH=CH—O—;

where ⋯ is a single or double bond and where $X_{11}$ is phenyl or phenyl substituted with one thru three $C_1$–$C_4$ alkyl, one thru three $C_1$–$C_4$ alkoxy, one phenyl, one thru three —F, —Cl, —Br and —I and compound (XVIII)

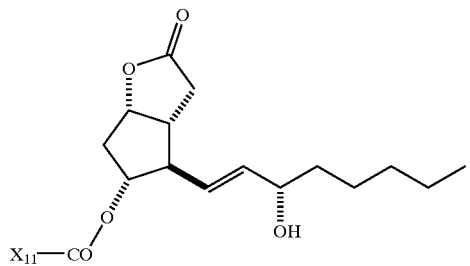

where $X_{11}$ is defined above which comprises:

(2) contacting a compound selected from the group consisting of compound (III)

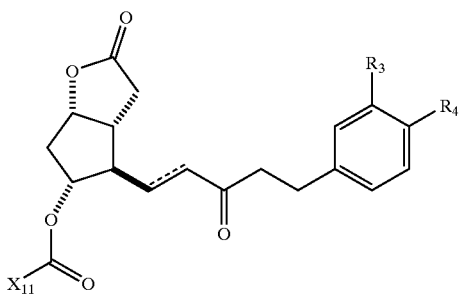

where $R_3$, $R_4$, $X_{11}$ and ⋯ are as defined above or compound (XVII), respectively,

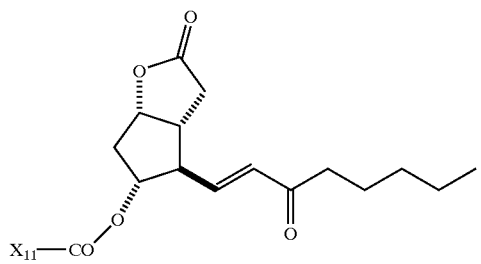

where $X_{11}$ is defined above with (−)-chlorodiisopinocampheylborane while maintaining the reaction mixture temperature in the range of from about −50° to about 0° and (2) contacting the reaction mixture of step (1) with a boron complexing agent.

6. A process according to claim 5 where the reaction mixture temperature is less than −20°.

7. A process according to claim 6 where the reaction mixture temperature is from about −35 to about −45°.

8. A process according to claim 5 where about 3 to about 4 equivalents of (−)-chlorodiisopinocampheylborane are used.

9. A process according to claim 8 where at least 3.5 equivalents of (−)-chlorodiisopinocampheylborane are used.

10. A process according to claim 5 where prior to step (2), the reaction mixture of step (1) is contacted with a readily reducible aldehyde or ketone.

11. A process according to claim 10 where the readily reducible aldehyde or ketone is selected from the group consisting of $C_1$–$C_6$ aldehydes and ketones and benzaldehyde.

12. A process according to claim 11 where the readily reducible aldehyde or ketone is acetone or methylethylketone.

13. A process according to claim 5 where the boron complexing agent is selected from the group consisting of water, $C_1$–$C_6$ alcohols and diols, ethanolamine, diethanolamine, triethanolamine and mixtures thereof.

14. A process according to claim 13 where the boron complexing agent is selected from the group consisting of water and diethanolamine.

15. A process according to claim 14 where the boron complexing agent is water.

16. A process according to claim 15 where base is added with the boron complexing agent.

17. A process according to claim 16 where the base is selected from the group consisting of carbonate, bicarbonate, mono- di- and tri-$C_1$–$C_6$ alkylamines, pyridine and pyridine substituted with $C_1$–$C_4$ alkyl.

18. A process according to claim 17 where the base is bicarbonate or carbonate.

19. A process according to claim 5 where prior to, or after, step (2), the reaction mixture is warmed to about 15 to about 25°.

20. A process according to claim 19 where the where the reaction mixture is warmed from about 1 to about 3 hr.

21. A process according to claim 5 where $X_{11}$ is phenyl.

22. A process according to claim 5 where the 15(S)-prostaglandin intermediate is compound (IV)

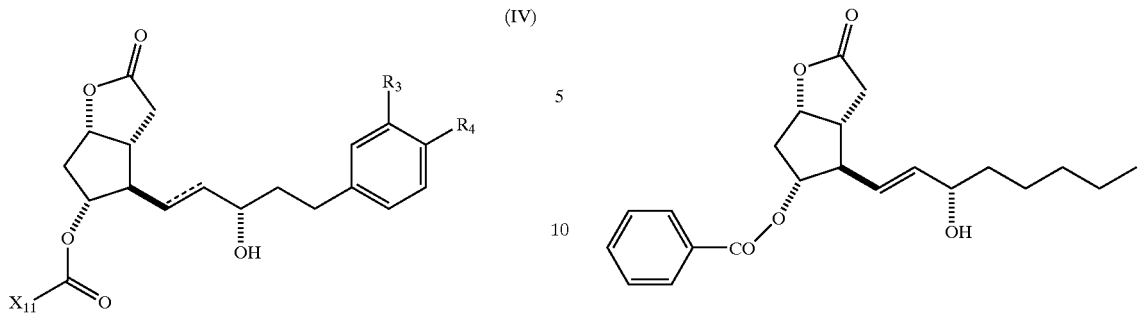
known as [3aR-[3aα,4a(1E,3S*),5β,6aα]]-5-(benzoyloxy) hexahydro-4-(3-hydroxy-5-phenyl-1-pentenyl)-2H-cyclopenta[b]furan-2-one.
23. A process according to claim 5 where the 15(S)-prostaglandin intermediate is compound (XVIII)
known as [3aR-[3aα,4α(E),5β,6aα]]-5-(benzoyloxy) hexahydro-4-(3-hydroxy-1-octenyl)-2H-cyclopenta[b]furan-2-one.
* * * * *

UNITED STATES PATENT AND TRADEMARK OFFICE
CERTIFICATE OF CORRECTION

PATENT NO. : 6,689,901 B2
DATED : February 10, 2004
INVENTOR(S) : Kevin E. Henegar It is certified that error appears in the above-identified patent and that said Letters Patent is hereby corrected as shown below:

Title page,
Item [57], ABSTRACT, second line under Formula VI: currently reads "of a 15(S) prostaglandin" and should read -- of a prostaglandin --

Column 1,
Lines 20 and 22, currently reads "(Example 2)" and should read -- (Example 9) --
Line 30, currently reads "eantiomeric" and should read -- enantiomeric --
Line 66, currently reads "of a 15(S) prostaglandin" and should read -- of a prostaglandin --

Column 2,
Line 31, under the formula insert -- XVIII --
Line 63, under the formula insert -- XVII --

Column 3,
Line 7, currently reads "Example 2" and should read -- Example 9 --
Line 8, currently reads "fort" and should read -- forth --
Line 66, currently reads "step (2), the" and should read -- step (2) of Claim 5, the --
Line 67, currently reads "of step (1) is" and should read -- of step (1) of Claim 5 is --

Column 4,
Line 45, currently reads "Latanoprost (XVI) refers" and should read -- Latanoprost refers --
Line 45, currently reads "(5Z)-(9Cl)-7-" and should read -- (5Z)-7- --
Lines 47-48, delete the sentence which currently reads "It is also known as 17-phenyl-18,19,20-trinor-PF2a isopropylester."

Column 7,
Line 5, currently reads "(10)" and should read -- (10 g) --

Column 8,
Line 47, currently reads "washed once with" and should read -- washed with --
Line 47, currently reads "acetate (15 mL)." and should read -- acetate (3 × 15 mL) --

Column 9,
Line 10, currently reads "(5Z)-(9Cl)-7-" and should read -- (5Z)-7- --

Column 17,
Line 1, currently reads "of a 15(S)-prostaglandin" and should read -- of a prostaglandin --

UNITED STATES PATENT AND TRADEMARK OFFICE
CERTIFICATE OF CORRECTION

PATENT NO. : 6,689,901 B2
DATED : February 10, 2004
INVENTOR(S) : Kevin E. Henegar It is certified that error appears in the above-identified patent and that said Letters Patent is hereby corrected as shown below:

Column 17 (cont'd),
Line 49, currently reads "(2)" and should read -- (1) --

Column 18,
Line 66, currently reads "the 15(S)-prostaglandin" and should read -- the prostaglandin --

Column 19,
Lines 18-19, currently reads "the 15(S)-prostaglandin" and should read -- the prostaglandin --

Signed and Sealed this

Twentieth Day of July, 2004

JON W. DUDAS
*Acting Director of the United States Patent and Trademark Office*